United States Patent [19]

Nedelec et al.

[11] 4,396,614
[45] Aug. 2, 1983

[54] NOVEL STEROIDS

[75] Inventors: Lucien Nedelec, Le Raincy; Vesperto Torelli, Maisons-Alfort; Daniel Philibert, La Varenne Saint-Hilaire, all of France

[73] Assignee: Roussel Uclaf, Paris, France

[21] Appl. No.: 332,842

[22] Filed: Dec. 21, 1981

[30] Foreign Application Priority Data

Dec. 23, 1980 [FR] France .................. 80 27272

[51] Int. Cl.³ .......................... A61K 31/58
[52] U.S. Cl. .................. 424/241; 260/239.57; 260/397.1; 260/397.4
[58] Field of Search .......... 260/239.57, 397.1, 397.4

[56] References Cited

U.S. PATENT DOCUMENTS 3,053,840 9/1962 Brown ................... 260/239.57
4,258,039 3/1981 Nedelec et al. ......... 260/239.57

Primary Examiner—Elbert L. Roberts
Attorney, Agent, or Firm—Hammond & Littell, Weissenberger and Muserlian

[57] ABSTRACT

Novel steroids of the formula

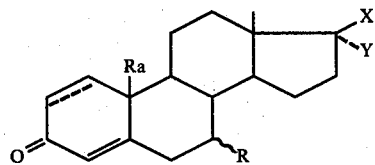

wherein R is selected from the group consisting of $R_1$ and $R_2$, $R_1$ is selected from the group consisting of alkyl of 1 to 8 carbon atoms and alkenyl and alkynyl of 2 to 8 carbon atoms $R_2$ is —(CH$_2$)$_n$—$R_3$, n is an integer from 1 to 8 and $R_3$ is selected from the group consisting of free or protected —OH, free or protected —NH$_2$, monoalkyl and dialkylamino with 1 to 6 carbon atoms, a free, esterified or salified —COOH and halogen X and Y together form

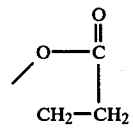

or X is OH and Y is —CH$_2$—CH$_2$—COOM, M is selected from the group consisting of hydrogen, an alkali metal and —NH$_4$, Ra is selected from the group consisting of hydrogen and methyl, the dotted line in the I(2)-position indicates the optional presence of a double bond and the wavy line indicates that R may be in the α- or β-position, with the proviso that R is not $R_1$ or $R_2$ when n is 1 and $R_3$ is halogen, when the 1(2) bond is a simple bond and when Ra is —CH$_3$, $R_3$ is not a free carboxyl when Y is —CH$_2$—CH$_2$—COOM in which M is an alkali metal or —NH$_4$ and $R_3$ is not a salified carboxyl when Y is —CH$_2$—CH$_2$—COOH having aldosterone antagonistic properties and increases aqueous sodium diuresis while conserving organic potassium without secondary hormonal effects and their preparation.

36 Claims, No Drawings

NOVEL STEROIDS

STATE OF THE ART

French Pat. No. 2,255,914 describes γ-lactones of 7-halomethyl-17α-Δ⁴-pregne-17-ol-3-one-21-carboxylic acids which do not contain any 1(2) unsaturation having antiprogestative activity. French Pat. No. 2,150,852 describes γ-lactones of 7-alkoxy carbonyl-17α-Δ⁴-pregnene-17β-ol-3-one-21-carboxylic acids having diuretic activity. Atwater et al. [J. of Organic Chemistry, Vol. 26 No. 9 (1961), p. 3077–3083] describes steroidal aldosterone antagonists different from the compounds of the present invention. Commonly assigned U.S. Pat. No. 4,258,039 discloses different steroidal lactones.

OBJECTS OF THE INVENTION

It is an object of the invention to provide the novel steroids of formula I and a novel process for their preparation.

It is another object of the invention to provide novel compositions to combat cardiac insufficiencies and arterial hypertension as well as a novel method for treating the same.

These and other objects and advantages of the invention will become obvious from the following detailed description.

THE INVENTION

The novel compounds of the invention are steroids of the formula

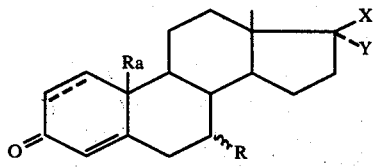

wherein R is selected from the group consisting of $R_1$ and $R_2$, $R_1$ is selected from the group consisting of alkyl of 1 to 8 carbon atoms and alkenyl and alkynyl of 2 to 8 carbon atoms $R_2$ is —$(CH_2)_n$—$R_3$, n is an integer from 1 to 8 and $R_3$ is selected from the group consisting of free or protected —OH, free or protected —$NH_2$, monoalkyl and dialkylamino with 1 to 6 carbon atoms, a free, esterified or salified —COOH and halogen X and Y together form

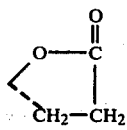

or X is OH and Y is —$CH_2$—$CH_2$—COOM, M is selected from the group consisting of hydrogen, an alkali metal and —$NH_4$, $R_a$ is selected from the group consisting of hydrogen and methyl, the dotted line in the 1(2)-position indicates the optional presence of a double bond and the wavy line indicates that R may be in the α- or β-position, with the proviso that R is not $R_1$ or $R_2$ when n is 1 and $R_3$ is halogen, when the 1(2) bond is a simple bond and when $R_a$ is —$CH_3$, $R_3$ is not a free carboxyl when Y is —$CH_2$—$CH_2$—COOM in which M is an alkali metal or —$NH_4$ and $R_3$ is not a salified carboxyl when Y is —$CH_2$—$CH_2$—COOH.

Among the preferred compounds of formula I' are steroids of the formula

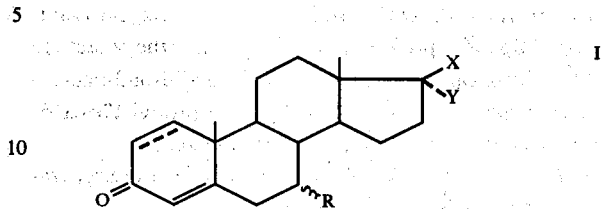

wherein R, X, Y, the dotted line and the wavy line have the above definition with the proviso that R is not $R_1$ or $R_2$ when n is 1 and $R_3$ is halogen, when the 1(2) bond is a simple bond, $R_3$ is not a free carboxy when Y is —$CH_2$—$CH_2$—COOM when M is an alkali metal or —$NH_4$ and $R_3$ is not salified carboxy when Y is —$CH_2$—$CH_2$—COOH.

Examples of R are alkyl such as methyl, ethyl, propyl, isopropyl, butyl, tert.-butyl, isobutyl, sec.-butyl, pentyl, isopentyl, sec.-pentyl, tert.-pentyl, neopentyl, linear or branched hexyl, heptyl and octyl; alkenyl such as vinyl, allyl, isopropenyl, butenyl, isobutenyl, or branched or linear pentenyl, hexenyl, heptenyl or octenyl; alkynyl such as ethynyl, propargyl or butynyl.

Examples of R as $R_2$ are —$(CH_2)_n$—$R_3$ wherein $R_3$ is tetrahydropyranyloxy, tert.-butoxy or benzyloxy or monoalkylamino and dialkylamino such as methylamino, ethylamino, n-propylamino, dimethylamino, diethylamino, di-n-propylamino, diisopropylamino or methylethylamino. When $R_3$ is a protected amino, it is preferably tritylamino, benzylamino, tert.-butylamino or tert.-pentylamino.

When $R_3$ is an esterified carboxy, the alcohol moiety is preferably alkyl of 1 to 4 carbon atoms such as methyl, ethyl, propyl, isopropyl, butyl, isobutyl, sec.-butyl or tert.-butyl or aralkyl such as benzyl or haloalkyl of 1 to 4 carbon atoms such as 2-chloroethyl, 2-bromoethyl, 2-iodoethyl or β,β,β-trichloroethyl. When $R_3$ is a halogen, it is preferably chlorine or bromine.

When $R_3$ is a salified carboxy, the salifying ion may be an alkali metal, an alkaline earth metal, —$NH_4$ or an organic amine. Examples are alkali metals such as sodium, potassium or lithium, alkaline earth metals such as calcium or magnesium and organic amines such as methylamine, propylamine, trimethylamine, N,N-dimethylethanolamine and tris(hydroxymethyl)amino methane. When M is an alkali metal, it is preferably sodium, potassium or lithium.

Among the preferred compounds of formula I' are those wherein $R_a$ is methyl, R is $R_2$ and the 1(2)-dotted line is a simple bond, those wherein Ra is hydrogen and the 1(2) dotted line is a simple bond, those wherein the 1(2) dotted line is a double bond, those wherein X and Y form

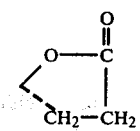

and those wherein X is —OH and Y is —$CH_2$—$CH_2$—COOK. While the R group may be in one of the 2 possible positions, the 7α-position is preferred.

Among the more preferred compounds of formula I' are those wherein R is selected from the group consisting of propyl, butyl, isobutyl, butenyl, chloropropyl, hydroxypropyl, carboxyethyl and methoxycarbonylethyl. Specific preferred compounds are the γ-lactone of 7α-propyl-17α-Δ$^{1,4}$-pregnadiene-17β-ol-3-one-21-carboxylic acid and potassium 7α-propyl-17α-Δ$^{1,4}$-pregnadiene-17β-ol-3-one-21-carboxylate.

The novel process of the invention for the preparation of steroids of the formula

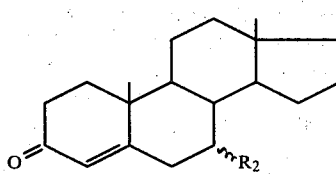

comprises reacting a compound of the formula

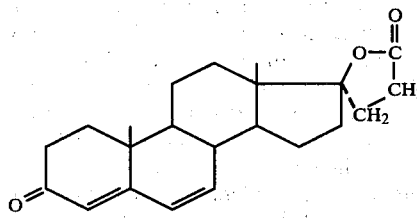

with either a compound of the formula

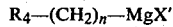

$R_4$—$(CH_2)_n$—$MgX'$   III$_1$ in the presence of a copper salt wherein X' is a halogen and $R_4$ is selected from the group consisting of protected —OH, protected amino and monoalkylamino and dialkylamino and n is 1 to 8 or with a compound of the formula

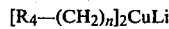

[$R_4$—$(CH_2)_n$]$_2$CuLi   III$_1'$ wherein $R_4$ and n have the above definitions to obtain after treatment with an acid a compound of the formula

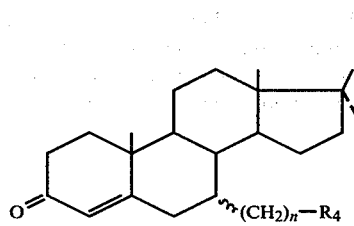

in the form of a mixture of 7α- and 7β-isomers which, if desired, may be separated and, if desired, each isomer or the mixture thereof when $R_4$ is protected —OH or protected amino may be treated with a hydrolysis agent to obtain a compound of the formula

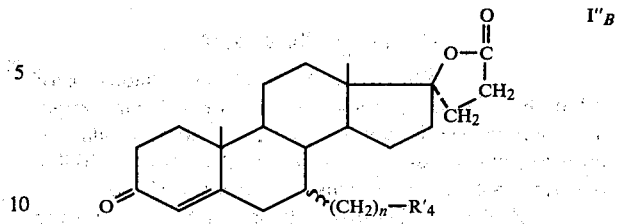

wherein $R_4'$ is selected from the group consisting of —OH and —NH$_2$ and when $R_4'$ is —OH, reacting the compound of formula I$_B''$ with an oxidizing agent to obtain a comound of the formula

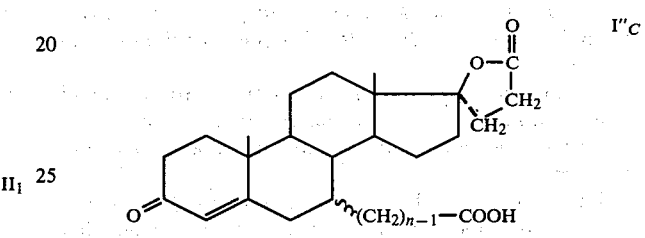

which may be esterified or salified by known methods or when n is other than 1, the compound of formula I$_B''$ is reacted with a halogenation agent to obtain a compound of the formula

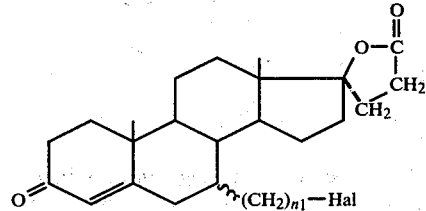

wherein $n_1$ is a integer from 2 to 8 and Hal is a halogen and, if desired, the compounds of formulae I$_A''$, I$_B''$, I$_C''$ or I$_D''$ in their 7α- or 7β-isomer form or mixtures thereof may be reacted with an alkali metal hydroxide or ammonium hydroxide to obtain a compound of the formula

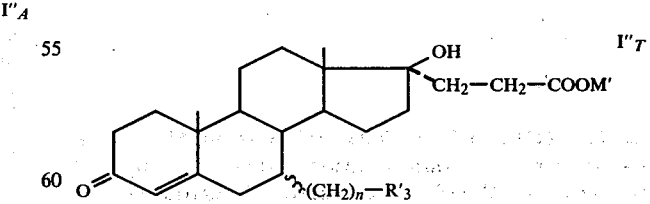

wherein $R_3'$ is $R_3$ other than free carboxy and M' is an alkali metal or —NH$_4$ in the form of its 7α- or 7β-isomers or mixtures thereof which, if desired, may be separated and then reacting the same with an acid agent to obtain a compound of the formula

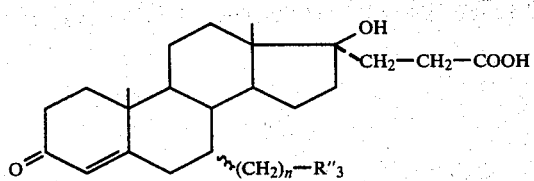

wherein R$_3''$ is R$_3$ other than salified carboxy.

The novel process of the invention for the preparation of steroids of the formula

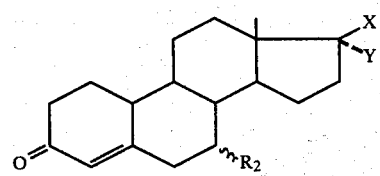  I''$_2$ comprises reacting a compound of the formula

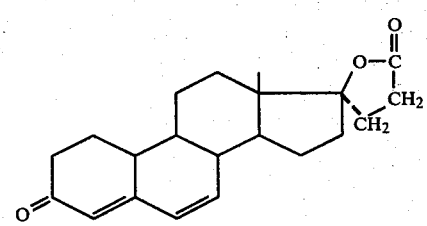  II$_2$ with either a compound of the formula

R$_5$—Mg—X'  III$_2$ in the presence of a copper salt wherein R$_5$ is R$_1$ or R$_4$—(CH$_2$)$_n$— and X' is a halogen or with a compound of the formula (R$_5$)$_2$CuLi  III$_2'$ to obtain after treatment with an acid a compound of the formula

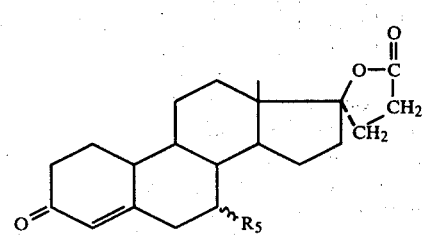  I''$_{A1}$ in the form of its 7α- and 7β-isomers which, if desired, may be separated and, if desired, each isomer or a mixture thereof when R$_5$ is —(CH$_2$)$_n$—R$_4$ and R$_4$ is a protected amino or protected —OH reacted with a hydrolysis agent to obtain a compound of the formula

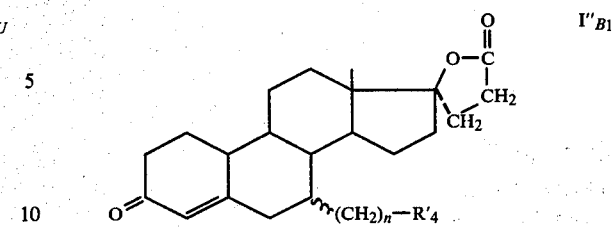  I''$_{B1}$ wherein R$_4'$ is —OH or —NH$_2$ and reacting a compound of formula I$_{B1}''$ wherein R$_4'$ is —OH with either an oxidation agent when n is greater than 1 to obtain a compound of the formula

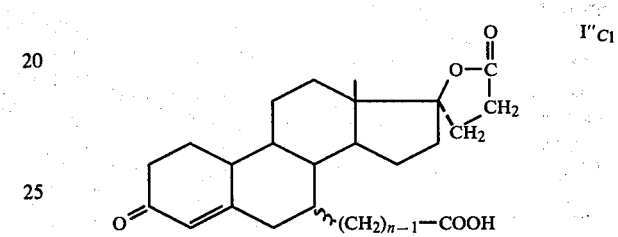  I''$_{C1}$ which is optionally esterified or salified by known methods or reacting the compound of formula I$_{B1}''$ with a halogenation agent to obtain a compound of the formula

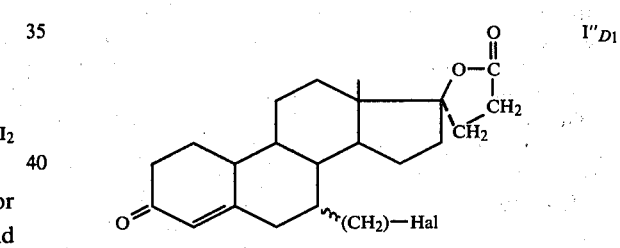  I''$_{D1}$ wherein Hal is a halogen and, if desired, reacting the compounds of formulae I$_{A1}''$, I$_{B1}''$, I$_{C1}''$ or I$_{D1}''$ in the form of their 7α- or 7β-isomers or mixtures thereof with an alkali metal hydroxide or ammonium hydroxide to obtain a compound of the formula

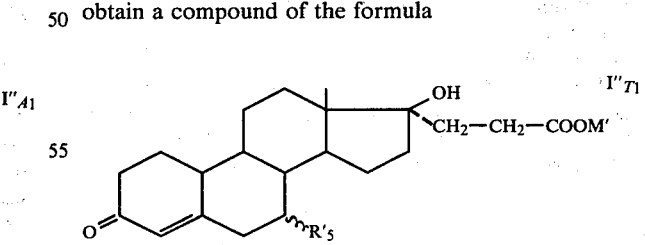  I''$_{T1}$ wherein R$_5''$ has the definition of R$_1$ or is —(CH$_2$)$_n$—R$_3'$ wherein R$_3'$ is R$_3$ with the exception of free carboxyl and M' is alkali metal or —NH$_4$ or the form of its 7α- or 7β-isomers or mixtures thereof which can be separated into its isomers if desired and subjecting the compound of formula I$_{T1}''$ to an acid agent to obtain a compound of the formula

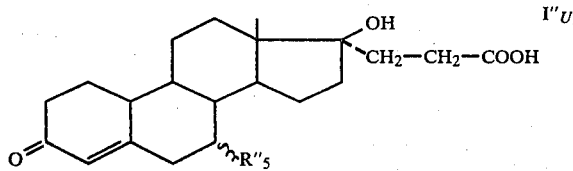

wherein $R_5''$ is $R_1$ or $-(CH_2)_n-R_3''$ and $R_3''$ is $R_3$ except for salified carboxy.

In a preferred embodiment of the process of the invention, the compound of the formula

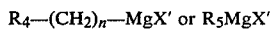

has X' as chlorine, bromine or iodine and the copper salt used is cupric chloride, bromide or acetate or cuprous chloride, bromide or iodide. The preferred acid to obtain a compound of formula $I_A''$ or $I_{A1}''$ is hydrochloric acid, nitric acid or sulfuric acid and the separation of the isomeric mixtures is effected by chromatography of fractional crystallization. The hydrolysis of the compounds of formula $I_A''$ or $I_A''$ is preferably with hydrochloric acid, p-toluene sulfonic acid or trifluoroacetic acid.

The optional oxidation of the products of formula $I_B''$ or $I_{B1}''$ is preferably with chromic oxide but equally useful are chromic reactants in general such as Heilbron reactant which is an aqueous solution of chromic oxide and sulfuric acid. The optional esterification of the acids of formula $I_C'$ or $I_{C1}''$ is effected under known conditions such as by reaction with a diazoalkane or with an alcohol in the presence of an acid such as p-toluene sulfonic acid. The optional salification of the said acids may be obtained by known methods such as reaction with an organic or inorganic base or a salt of an organic or inorganic acid.

The preparation of the products of formula $I_D''$ or $I_{D1}''$ is preferably effected by reaction with gaseous hydrogen halide or in the presence of sulfuric acid. Equally useful is a mixture of zinc chloride and hydrochloric acid or thionyl chloride to form the chloride derivative or with triphenylphosphine in the presence of carbon tetrachloride as taught in Canadian Journal of Chemistry, Vol. 76 (1968), p. 86.

The alkali metal hydroxide used to optionally treat a compound of formula $I_A''$, $I_B''$, $I_C''$, $I_D''$, $I_{A1}''$, $I_{B1}''$, $I_{C1}''$ or $I_{D1}''$ is preferably sodium hydroxide or potassium hydroxide. The acid used to optionally treat a compound of formula $I_T''$ or $I_{T1}''$ is hydrochloric acid, sulfuric acid, nitric acid or acetic acid.

The novel process of the invention for the preparation of compounds of formula I' wherein the 1(2)-position contains a double bond comprises reacting a compound of the formula

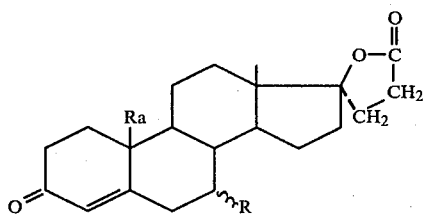

wherein R is $R_1$ or $R_2$ and Ra, $R_1$ and $R_2$ have the above definitions in the form at its 7α- or 7β-isomers or mixtures thereof with a dehydrogenation agent to obtain a compound of the formula

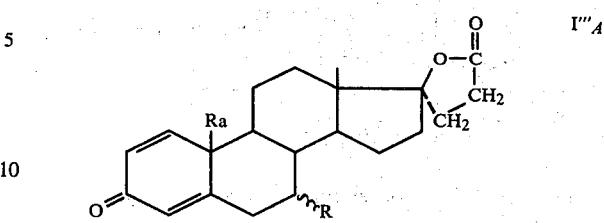

in the form of its 7α- or 7β-isomers or mixtures thereof which can optionally be separated and reacting the latter with an alkali metal hydroxide or ammonium hydroxide to obtain a compound of the formula

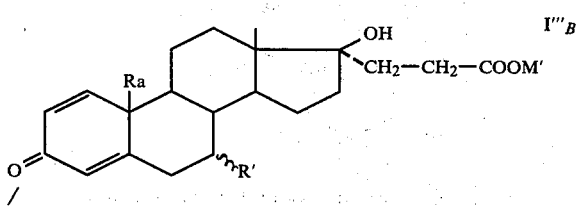

wherein M' is an alkali metal or $-NH_4$ and R' is R except for free carboxy in the form of its 7α- or 7β-isomers or mixtures thereof which, if desired, may be separated and subjecting the latter to an acid agent to form a compound of the formula

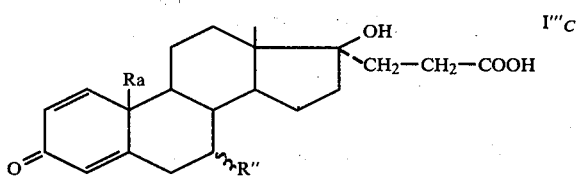

wherein R" is R except for $(CH_2)_n-R_3$ and $R_3$ is salified carboxy.

The transformation of a compound of formula IV into a compound of formula $I_A'''$ is preferably effected biochemically with Anthrobacter Simplex bacteria or another microorganism. In this instance, the reaction is preferably effected in a buffered aqueous medium and for solubility reasons, the salt of the product of formula IV with a base such as sodium hydroxide or potassium hydroxide is used. When the reaction with the microorganism is used, the product of formula $I_A'''$ is obtained by acidification of a solution of an intermediate salt thereof such as hydrochloric acid, sulfuric acid or acetic acid. When the said transformation is effected chemically, it is preferred to use a derivative of p-benzoquinone or chloranil in an organic solvent such as dioxane, acetone, benzene or tert.-butanol. Equally useful as a dehydrogenation agent is selenous anhydride or selenic benzene anhydride. The transformation of the products of formula $I_A'''$ into products of formula $I_B'''$ and the optional separation of the isomer and acidification to obtain the products of formfula $I_C'''$ is realized as described above.

The novel compositions of the invention having aldosterone antagonistic activity and capable of increasing aqueous sodium diuresis while conserving organic potassium are comprised of an effective amount of at least one compound of formula I" and an inert pharmaceutical carrier or excipient. The compositions may be in the form of tablets, dragees, cachets, capsules, granules, emulsins, syrups, suppositories or injectable solutions or suspensions prepared in the usual manner.

Example of suitable excipients are talc, arabic gum, lactose, starch, magnesium stearate, cacao butter, aqueous or non-aqueous vehicles, fatty bodies of animal or vegetable origin pariffinic derivatives, glycols, diverse wetting agents, dispersants or emulsifiers and preservatives.

The compositions of the invention do not prevent any secondary hormonal side effects and tests effected with the receptor and in vivo particularly show that the compounds of formula I' have less antiandrogenic activity than previously described compounds. The compounds of the invention are useful for combatting arterial hypertension and cardiac insufficiencies.

Among the preferred compositions of the invention are those wherein Ra is methyl, R is $R_2$ and the 1(2)-dotted line is a simple bond, those wherein Ra is hydrogen and the 1(2) dotted line is a simple bond, those wherein the 1(2) dotted ine is a double bond, those wherein X and Y form

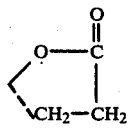

and those wherein X is —OH and Y is —$CH_2$—$CH_2$—COOK. While the R group may be in one of the 2 possible positions the 7α-position is preferred.

Among the more preferred compounds of formula I' are those wherein R is selected from the group consisting of propyl, butyl, isobutyl, butenyl, chloropropyl, hydroxypropyl, carboxyethyl, and methoxycarboxylethyl. Specific preferred compounds are γ-lactone of 7α-propyl-17α-$\Delta^{1,4}$-pregnadiene-17β-ol-3-one-21-carboxylic acid and potassium 7α-propyl-17α-$\Delta^{1,4}$-pregnadiene-17β-ol-3-one-21-carboxylate.

The novel method of the invention for combatting arterial hypertension and cardiac insufficiency comprises administering to warm-blooded animals, including humans, an amount of at least one compound of formula I' to combat cardiac insufficiency and arterial hypertension. The compounds may be administered orally, rectally, transcutaneously or intraveinously and the usual daily dose in 0.05 to 10 mg/kg depending on the compound and method of administration. For example, the daily oral dose of the compound of Example 10 is 0.2 to 10 mg/kg.

The starting materials of formula II are known compounds and may be prepared by the processes described in U.S. Pat. No. 3,194,803 or French Pat. No. 2,216,276. The compounds of formula IV wherein Ra is methyl and R is optionally unsaturated alkyl of 2 to 8 carbon atoms may be prepared by the process described in published EPC application No. 0018245. The compounds of formula IV wherein R and Ra are methyl are descibed in J. Org. Chem. Soc., Vol. 26 (1961), p. 3077-83. The other products of formula IV fall within the products of formula I'' by the indicated process of preparation.

In the following examples there are described several preferred embodiments to illustrate the invention. However, it is to be understood that the invention is not intended to be limited to the specific embodiments.

EXAMPLE 1

γ-lactone of 7α-propyl-$\Delta^{1,4}$-17α-pregnadine-17β-ol-3-one-21-carboxylic acid A mixture of 2 g of the γ-lactone of 7α-propyl-$\Delta^4$-17α-pregnene-17β-ol-3-one-21-carboxylic acid, 1.44 g of 2,3-dichloro-5,6-dicyano-1,4-benzoquinone and 10 ml of dioxane was refluxed under an inert atmosphere for 105 minutes and was iced for 10 minutes and was vacuum filtered. The filter was rinsed with dioxane and the filtrate was washed with an aqueous 10% sodium thiosulfate solution, then with N ammonium hydroxide solution and the wash waters were extracted with ethyl acetate. The combined organic phases were dried and evaporated to dryness under reduced pressure to obtain 2.8 g of residue. The latter was chromatographed over silica gel and was eluted with an 8-2 benzene-ethyl acetate mixture to obtain 1.4 g of product which was crystallized from 5 ml of ether. The mixture was vacuum filtered to obtain 1.3 g of γ-lactone of 7α-propyl-$\Delta^{1,4}$-17α-pregnadiene-17β-ol-3-one-21-carboxylic acid which after crystallization from isopropanol melted at 202° C. and a specific rotation of $[\alpha]_D^{20} = +3° \pm 2°$ (c=0.8% in $CHCl_3$).

Analysis: $C_{25}H_{34}O_3$; molecular weight=382.52. Calculated: %C, 78.49; %H, 8.96., Found: %C, 78.6; %H, 9.1.

EXAMPLE 2

γ-lactones of 7α-or 7β-[(1,1-dimethylethoxy)-propyl]-$\Delta^4$-pregnene-17β-ol-3-one-21-carboxylic acid 17 g of the γ-lactone of $\Delta^{4,6}$-pregnadiene-17β-ol-3-one-21-carboxylic acid or canrenone were added under an inert atmosphere to a mixture of 1.36 of cupric chloride, 0.860 g of lithium chloride, 150 ml of anhydrous ether and 150 ml of anhydrous tetrahydrofuran and then 105 ml of a solution of 0.68N 1,1-dimethylethoxypropyl magnesium chloride in tetrahydrofuran was added thereto dropwise with stirring over one hour at −30° C. The mixture was stirred at −30° C. for 30 minutes and then 100 ml of 5N hydrochloric acid were added thereto. The mixture was stirred for 5 minutes while allowing the temperature to rise to room temperature and was then poured into 250 ml of 2N ammonium hydroxide solution. The decanted aqueous phase was extracted with ether and the organic phase was washed with 0.5N ammonium hydroxide solution, then with water, dried and filtered. The filtrate was evaporated to dryness to obtain 23 g of residue which was chromatographed over silica gel. Elution with an 85-15 ether-benzene mixture yielded 13.7 g of γ-lactone of 7α-[(1,1-dimethylethoxy)-propyl]-$\Delta^4$-pregnene-17β-ol-3-one-21-carboxylic acid with an Rf=0.45 and 5.1 g of γ-lactone of 7β-[(1,1-dimethylethoxy)-propyl]-$\Delta^4$-pregnene-17β-ol-3-one-21-carboxylic acid with an Rf=0.35. The 7α-isomer was cyrstallized from isopropyl ether and was vacuum filtered to obtain 11.1 g of the said isomer melting at 118° C., 5 g of the latter was then crystallized from a 1-1 ether-ispropyl ether mixture to obtain 4.2 g of the pure isomer with a specific rotation of $[\alpha]_D^{20} = +55° \pm 1.5°$ (c=1.3% in chloroform).

Analysis: $C_{29}H_{44}O_4$; molecular weight=456.64-7α-isomer. Calculated: %C, 76.27; %H, 9.71. Found: %C, 76.4; %H, 9.8.

NMR Spectrum (deuterchloroform): 7α-isomer—Peaks at 1 ppm (18-methyl); at 1.19 ppm (t-butyl of 7α-propyl); at 1.225 ppm (19-methyl); at 3.3 ppm (t) (methyl adjacent to 7α-tert.-butyl (J=6 Hz)); 5.74 ppm (4-hydrogen). 7β-isomer—Peaks at 1.18 ppm (19-methyl); at 5.71 ppm (4-hydrogen); at 3.3 ppm (t) (methylene adjacent to 7β-tert.-butyl).

EXAMPLE 3

γ-lactone of 7α- and 7β-(3-hydroxypropyl)-17α-Δ$^4$-pregnene-17β-ol-3-one-21-carboxylic acid A solution of 9.5 g of the 7α-isomer of Example 2, 19 ml of dioxane and 28.5 ml of 22° Bé hydrochloric acid was stirred under an inert atmosphere at room temperature for 90 minutes and was then poured into 150 ml of water. The mixture was extracted with ethyl acetate and the organic phase was washed with aqueous sodium bicaronate, then with water, was dried and filtered. The filtrate was evaporated to dryness under reduced pressure and the residue was chromatographed over silica gel. Elution with a 1-1 benzene-methyl ethyl ketone mixture yielded 7 g of γ-lactone of 7α-(3-hydroxypropyl)-17α-Δ$^4$-pregene-17β-ol-3-one-21-carboxylic acid which melted at 208° C. after crystallization from ethyl acetate and a specific rotation of $[\alpha]_D^{20} = +61.5° \pm 1.5°$ (c=1% in chloroform).

Analysis: $C_{25}H_{36}O_4$; molecular weight=400.54. Calculated: %C, 74.96; %H, 9.06. Found: %C, 75.0; %H, 9.1.

2.7 g of the 7β-isomer of Example 2 was subjected to identical reaction conditions to obtain 1.7 g of γ-lactone of 7β-(3-hydroxypropyl)-17αΔ$^4$-pregnene-17β-ol-3-one-21-carboxylic acid which after crystallization from ethyl acetate melted at 192° C. and had a specific rotation of $[\alpha]_D^{20} = +59° \pm 1.5°$ (c=1% in chloroform).

Analysis: $C_{25}H_{36}O_4$; molecular weight=400.54. Calculated: %C, 74.96; %H, 9.06. Found: %C, 74.9, %H, 9.1.

EXAMPLE 4

γ-lactone of 7α-carboxyethyl-17α-Δ$^4$-pregnene-17β-ol-3-one-21-carboxylic acid

A solution of 1.5 g of the 7α-isomer of Example 3 and 45 ml of acetone under an inert atmosphere was cooled to 5° C. and 1.5 g of 8N Heilbron reagent (a mixture of 270 g of chromic oxide, 400 ml of water and 230 ml of sulfuric acid and sufficient additional water for a volume of one liter) were added thereto. The mixture was stirred at 5° C. for 30 minutes and was then poured into 50 ml of water. The mixture was extracted with ethyl acetate and the organic phase was washed with water. The organic phase was extracted with aqueous sodium bicarbonate solution and the aqueous extract was acidified with concentrated hydrochloric acid. The mixture was iced and vacuum filtered. The product was dried under reduced pressure to obtain 1.45 g of γ-lactone of 7α-carboxyethyl-17α-Δ$^4$-pregnene-17β-ol-3-one-21-carboxylic acid which melted at 205° C. The latter was crystallized from 20 ml of methanol to obtain 1.05 g melting at 205° C. and having a specific rotation of $[\alpha]_D^{20} = +43.5° \pm 1°$ (c=1% in chloroform).

Analysis: $C_{25}H_{34}O_5$; molecular weight=414.52. Calculated: %C, 72.43; %H, 8.27. Found: %C, 72.7; %H, 8.4.

EXAMPLE 5

γ-lactone of 7α-isopropoxycarbonylethyl-17α-Δ$^4$-pregnene-17β-ol-3-one-21-carboxylic acid

STEP A: O-isopropyl-N,N'-dicyclohexyl-isourea

A mixture of 3.09 g of dicyclohexylcarbodiimide, 30 mg of cuprous chloride and 994 mg of isopropanol was stirred under an inert atmosphere at 55° C. for 6 hours and was then diluted with ethyl acetate. The organic phase was washed with water, then with N ammonium hydroxide solution, was dried and filtered. The filtrate was evaporated to dryness under reduced pressure to obtain 3.2 g of O-isopropyl-N,N'-dicyclohexyl-isourea which was used as is for the next step.

STEP B: γ-lactone of 7α-isopropoxycarbonylethyl-17α-Δ$^4$-pregnene-17β-ol-3-one-21-carboxylic acid A mixture of 2 g of the acid of Example 4, 1.5 g of the product of Step A and 25 ml of dioxane was stirred under an inert atmosphere at 80° C. for 46 hours and was then iced and vacuum filtered. The filter was washed with methylene chloride and the filtrate was evaporated to dryness under reduced pressure. The 2.8 g of residue were chromatographed over silica gel and eluted with a 95-5 methylene chloride-dioxane mixture to obtain 1.85 g of γ-lactone of 7α-isopropoxycarbonylethyl-17α-Δ$^4$-pregnene-17β-ol-3-one-21-carboxylic acid which after crystallization from isopropyl ether resulted in 1.7 g of product which melted at 130° C. and had a specific rotation of $[\alpha]_D^{20} = +31.5° \pm 1.5°$ (c=1% in chloroform).

Analysis: $C_{28}H_{40}O_5$; molecular weight=456.60. Calculated: %C, 73.65; %H, 8.83. Found: %C, 73.6; %H, 8.8.

EXAMPLE 6

γ-lactone of 7α-methoxycarbonylethyl-17α-Δ$^4$-pregnene-17β-ol-3-one-21-carboxylic acid A solution of diazomethane in methylene chloride was added to a solution of 800 mg of the acid of Example 4 in 6 ml of chloroform and the mixture was stirred at room temperature for 15 minutes. The mixture was evaporated to dryness under reduced pressure and the residue was chromatographed over silica gel. Elution with an 85-15 ether-benzene mixture yielded 780 mg of γ-lactone of 7α-methoxycarbonylethyl-17α-Δ$^4$-pregnene-17β-ol-3-one-21-carboxylic acid. Crystallization of the latter from 2 ml of ethyl acetate yielded 610 mg of the γ-lactone melting at 147° C. and having a specific rotation of $[\alpha]_D^{20} = +44° \pm 1°$ (c=1% in CHCl$_3$).

Analysis: $C_{26}H_{36}O_5$; molecular weight=428.55. Calculated: %C, 72.86; %H, 8.47. Found: %C, 72.9; %H, 8.6.

EXAMPLE 7

γ-lactone of 7α-(3-chloropropyl)-17α-Δ$^4$-pregnene-17β-ol-3-one-21-carboxylic acid A solution of 4 g of the γ-lactone of the 7α-isomer of Example 3, 3.8 g of triphenylphosphine, 40 ml of carbon tetrachloride and 15 ml of chloroform was stirred under an inert atmosphere at reflux for 3 hours and was then filtered. The filter was washed with chloroform and the filtrate was evaporated to dryness under reduced pressure to obtain 8.99 g of residue. The latter was chromatographed over silica gel and eluted with a 1-1 benzene-methyl ethyl ketone mixture to obtain 3.5 g of product which was crystallized from ethyl acetate to obtain 3.2 g of γ-lactone of 7α-(3-chloropropyl)-17α-Δ⁴-pregnene-17β-ol-3-one-21-carboxylic acid melting at 202° C. and having a specific rotation of $[\alpha]_D^{20} = +60° \pm 1.5°$ (c=1% in chloroform).

Analysis: $C_{25}H_{35}ClO_3$; molcular weight=418.99. Calculated: %C, 71.66; %H, 8.42; %Cl, 8.46. Found: %C, 71.7; %H, 8.5; %Cl, 8.5.

EXAMPLE 8

γ-lactone of
7α-(3-chloropropyl)-17α-Δ¹,⁴-pregnadiene-17β-ol-3-one-21-carboxylic acid A solution of 3.5 g of the product of Example 7, 2.3 g of 2,3-dichloro-5,6-dicyano-1,4-benzoquinone and 17.5 ml of dioxane was refluxed with stirring under an inert atmosphere for 3 hours and was then iced for 10 minutes and was vacuum filtered. The filter was rinsed with dioxane and the filtrate was diluted with 30 ml of ethyl acetate, washed with 10% sodium thiosulfate solution and with 0.5N ammonium hydroxide solution. The mixture was reextracted with ethyl acetate and the organic phase was dried, filtered and evaporated to dryness under reduced pressure. The 4.7 g of residue were chromatographed over silica gel and eluted with an 8-2 benzene ethyl acetate mixture to obtain 2.4 of an oil. The latter was crystallized from 5 ml of ether to obtain 2.3 g of a product melting at 196° C. which was crystallized from isopropanol to obtain 1.9 g of γ-lactone of 7α-(3-chloropropyl)-17α-Δ¹,⁴-pregnadiene-17β-ol-3-one-21-carboxylic acid melting at 196° C. and having a specific rotation of $[\alpha]_D^{20} = +4° \pm 1.5°$ (c=0.8% in chloroform).

Analysis: $C_{25}H_{33}ClO_3$; molecular weight=416.97. Calculated: %C, 72.01; %H, 7.98; %Cl, 8.50. Found: %C, 72.0; %H, 8.1; %Cl, 8.7.

EXAMPLE 9

γ-lactone of
7α-(but-3-enyl)-17α-Δ¹,⁴-pregnadiene-17β-ol-3-one-21-carboxylic acid A solution of 4.7 g of the γ-lactone of 7α-(but-3-enyl)-17α-Δ⁴-pregnene-17β-ol-3-one-21-carboxylic acid, 3.5 g of 2,3-dichloro-5,6-dicyano-1,4-benzoquinone and 23.5 ml of dioxane was stirred at reflux under an inert atmosphere for 2½ hours and was then iced and vacuum filtered. The filtrate was rinsed with dioxane and the filtrate was diluted with 30 ml of dioxane. The mixture was washed with 10% aqueous sodium thiosulfate solution, with 0.5N ammonium hydroxide solution and then with water. The mixture was extracted with ethyl acetate and the organic phase was dried, filtered and evaporated to dryness under reduced pressure. The 5.2 g of oil residue were chromatographed over silica gel and were eluted with an 8-2 benzene-ethyl acetate mixture to obtain 1.8 g of product which was crystallized from ether to obtain 1.7 g of γ-lactone of 7α-(but-3-enyl)-17α-Δ¹,⁴-pregnadiene-17β-ol-3-one-21-carboxylic acid melting at 197° C. and having a specific rotation of $[\alpha]_D^{20} = -7° \pm 1°$ (c=0.9% in chloroform).

Analysis: $C_{26}H_{34}O_3$; molecular weight=394.53. Calculated: %C, 79.15; %H, 8.69. Found: %C, 79.3; %H, 8.8.

EXAMPLE 10

Potassium
7α-propyl-17α-Δ¹,⁴-pregnadiene-17β-ol-3-one-21-carboxylate

A suspension of 2 g of the ⸨-lactone of Example 1, 11.2 ml of 0.45N potassium ethanolate and 11.2 ml of water was refluxed under an inert atmosphere for 15 minutes and was then evaporated to dryness under reduced pressure. 50 ml of acetone were added to the residue and the mixture was iced and vacuum filtered. The 2 g of product melting at 280° C. were dissolved in a 1-1 mixture of water and moderately warm acetone and the solution was filtered, 70 ml of acetone were added to the filtrate and the mixture was iced and vacuum filtered to obtain 1.7 g of potassium 7α-propyl-17α-Δ¹,⁴-pregnadiene-17β-ol-3-one-21-carboxylate in the form of its monohydrate melting at 280° C. and a specific rotation of $[\alpha]_D^{20} = -20°35\,1°$ (c=1% in water).

Analysis: Monohydrated product—Calculated: %C, 65.75; %H, 8.17. Found: %C, 65.5; %H, 8.2.

Analysis: $C_{25}H_{35}KO_4$ (dried at 100° C.); molecular weight=438.63. Calculated: %C, 68.45, %H, 8.04. Found: %C, 68.2; %H, 8.0.

EXAMPLE 11

Potassium
7α-[1,1-(dimethylethoxy)-propyl]-17α-Δ⁴-pregnene-17β-ol-3-one-21-carboxylate Using the procedure of Example 10, 1.5 g. of the 7α-isomer of Example 2 were reacted to obtain 0.9 g of potassium 7α-[1,1-(dimethylethoxy)-propyl]-17α-Δ⁴-pregnene-17β-ol-3-one-21-carboxylate melting at >300° C. and having a specific rotation of $[\alpha]_D^{20} = +29.5° \pm 1.5°$ (c=1% in water)

Analysis: $C_{25}H_{45}KO_5$ (7.8% loss at 150° C. under reduced pressure); molecule weight=512.75. Calculated: %C, 67.93; %H, 8.85. Found: %C, 67.6; %H, 8.8. K. Fischer: 7.2 to 7.3% water

EXAMPLE 12

Potassium
7α-(3-hydroxypropyl)-Δ⁴-pregnene-17β-ol-3-one-21-carboxylate

Using the procedure of Example 10, 1.4 g of the product of Example 3 were reacted to obtain 0.95 g of potassium 7α-(3-hydroxypropyl)-Δ⁴-pregnene-17β-ol-3-one-21-carboxylate melting at >300° C. and having a specific rotation of $[\Delta]_D^{20} = +36.5° \pm 1.5°$ (c=1% in water).

Analysis: $C_{25}H_{37}KO_5$; molecular weight=456.65 (11.8% loss at 150° C. under vacuum). Calculated: %C, 65.75; %H, 8.17. Found: %C, 65.7; %H, 8.2. K. Fischer: 11.3 to 11.7% water

Example 13

Potassium
7α-(3-chloropropyl)-17α-Δ⁴-pregnene-17β-ol-3-one-21-carboxylate

Using the procedure of Example 10, 1.5 g of the product of Example 7 were reacted to obtain 1.25 g of potassium 7α-(3-chloropropyl)-17α-Δ⁴-pregnene-17β-ol-3-one-21-carboxylate melting at 325° C. and having a specific rotation of $[\alpha]_D^{20} = +38° \pm 1.5°$ (c=1% in water)

Analysis: $C_{25}H_{36}KO_4Cl$; molecular weight=475.11 (2.8% loss at 150° C. under vacuum). Calculated: %C, 63.20; %H, 7.64, %Cl, 7.46. Found: %C, 63.2; %H, 7.6; %Cl, 7.4.

K. Fischer: 4.7% water

EXAMPLE 14

Potassium 7α-(3-chloropropyl)-17α-Δ$^{1,4}$-pregnadiene-17β-ol-3-one-21-carboxylate Using the procedure of Example 10, 0.84 g of the product of Example 8 were reacted to obtain 0.62 g of potassium 7α-(3-chloropropyl)-17α-Δ$^{1,4}$-pregnadiene-17β-ol-3-one-21-carboxylate melting at 230° C. and having a specific rotation of $[\alpha_D^{20} = -22.5° \pm 1.5°$ (c=1.1% in water).

Analysis: $C_{25}H_{34}ClKO_4$; molecular weight=473.094 (solvate with 5% $H_2O$). Calculated: %C, 60.29; %H, 7.43; %Cl, 7.12. Found: %C, 60.4; %H, 7.0; %Cl, 7.2. K. Fischer: 4.7 to 5.2% water

EXAMPLE 15

Potassium 7α-(but-3-enyl)-17α-Δ$^{1,4}$-pregnadiene-17β-ol-3-one-21-carboxylate

Using the procedure of Example 10, 1.16 g of the product of Example 9 were reacted to obtain 0.634 g of potassium 7α-(but-3-enyl)-17α-Δ$^{1,4}$-pregnadiene-17β-ol-3-one-21-carboxylate melting at ≈270° C. and having a specific rotation of $[\alpha]_D^{20} = -32° \pm 1°$ (c=1% in water).

Analysis: $C_{26}H_{35}KO_4 \cdot \frac{1}{2} H_2O$; molecular weight=459.65 Calculated: %C, 67.93; %H, 7.89. Found: %C, 67.6; %H, 7.8.

K. Fischer: 1.9 to 2.1% water.

EXAMPLE 16

γ-lactone of 7α-propyl-17α-Δ$^{1,4}$-pregnadiene-17β-ol-3-one-21-carboxylic acid A suspension of 10 g of the γ-lactone of 7α-propyl-17α-Δ$^4$-pregnene-17β-ol-3-one-21-carboxylic acid, 60.5 ml of potassium methanolate and 60.5 ml of water was refluxed under an inert atmosphere for 15 minutes to obtain solution A containing potassium 7α-propyl-17α-Δ$^4$-pregnene-17β-ol-3-one-21-carboxylate. A buffered solution of 13.6 g of monopotassium phosphate in 1.9 liters of water was admixed with 60 ml of N sodium hydroxide solution and the pH of the mixture was adjusted to 7.2 by addition of 6.1 ml of N sodium hydroxide solution to obtain solution B. 1.5 liters of solution B were added to solution A and then 50 mg of menadione, 100 ml of enzymatic cream of Arthrobacter simplex and 10 g of hyflosupercel were added thereto. The suspension was stirred at 33°±1° C. while bubbling air therethrough for 24 hours and was then acidified by addition of 100 ml of 5N hydrochloric acid. The mixture was stirred at room temperature for 30 minutes and 400 ml of ethyl acetate were added. The mixture was stirred for 15 minutes and was filtered. The filter was rinsed with ethyl acetate and the decanted organic phase of the filtrate was washed with 10% aqueous sodium thiosulfate solution, with aqueous sodium bicarbonate solution and with water. The mixture was reextracted with ethyl acetate and the organic phase was dried, filtered and evaporated to dryness under reduced pressure to obtain 9.5 g of γ-lactone of 7α-propyl-17α-Δ$^{1,4}$-pregnadiene-17β-ol-3-one-21-carboxylic acid.

The hyflosupercel cake was suspended in 150 ml of methanol and the mixture was stirred for 30 minutes and was filtered. The filtrate was evaporated to dryness under reduced pressure and the residue was taken up in water. The mixture was extracted with ethyl acetate and the organic phase was dried, filtered and evaporated to dryness to obtain another 0.6 g of the desired product. Another extraction of the hyflosupercel with a 1-1 mixture of methylene chloride and methanol recovered another 140 mg of product.

The 3 yields of 10.2 g were combined and dissolved in 300 ml of ethyl acetate at 50° C. 41.5 g of activated carbon were added thereto and the mixture was stirred for 5 minutes and then filtered. The filtrate was evaporated to dryness under reduced pressure and the residue was taken up in 25 ml of isopropyl ether. The mixture was vacuum filtered to obtain 9.6 g of a product identical to that of Example 1 melting at 202° C.

EXAMPLE 17

γ-lactone of 7α-propyl-17α-Δ$^{1,4}$-pregnadiene-17β-ol-3-one-21-carboxylic acid A mixture of 1 g of the γ-lactone of 7α-propyl-17α-Δ$^4$-pregnene-17β-ol-3-one-21-carboxylic acid, 10 ml of anhydrous toluene and 1.1 g of selenic benzene anhydride was heated at 100° C. with stirring under an inert atmosphere for one hour and was then diluted with 30 ml of ethyl acetate. The organic phase was washed with aqueous sodium bicarbonate solution and the aqueous phase was extracted with ethyl acetate. The combined organic phases were dried, filtered and evaporated to dryness under reduced pressure. The 1.25 g of oil were chromatographed over silica gel and eluted with an 8-2 benzene-ethyl acetate mixture to obtain 850 mg of γ-lactone of 7α-propyl-17α-Δ$^{1,4}$-pregnadiene-17β-ol-3-one-21-carboxylic acid melting at 202° C. and identical to the product of Examples 1 and 16.

EXAMPLE 18

γ-lactone of 7α-butyl-17α-Δ$^{1,4}$-pregnadiene-17β-ol-3-one-21-carboxylic acid

Using the procedure of Example 16, 2 g of the γ-lactone of 7α-butyl-17α-Δ$^4$-pregnene-17β-ol-3-one-21-carboxylic acid were reacted to obtain 1.6 g of γ-lactone of 7α-butyl-17α-Δ$^{1,4}$-pregnadiene-17β-ol-3-one-21-carboxylic acid melting at 183° C. and having a specific rotation of $[\alpha]_D^{20} = -9.5° \pm 2°$ (c=0.7% in chloroform).

Analysis: $C_{26}H_{36}O_3$; molecular weight=396.5. Calculated: %C, 78.74; %H, 9.15. Found: %C, 79.0; %H, 9.3.

EXAMPLE 19

γ-lactone of 7α-(2-methylpropyl)-17α-Δ$^{1,4}$-pregnadiene-17β-ol-3-one-21-carboxylic acid Using the procedure of Example 16, 1 g of the γ-lactone of 7α-(2-methylpropyl)-17α-Δ$^4$-pregnene-17β-ol-3-one-21-carboxylic acid was reacted to obtain a first yield of 0.9 g of product. The hyflosupercel cake was taken up in methylene chloride and the mixture was filtered. The filtrate was washed with aqueous sodium bicarbonate solution, was dried, filtered and evaporated to dryness under reduced pressure to obtain another 0.2 g of product. The combined yields were chromatographed over silica gel and eluted with an 8-2 benzene-ethyl acetate mixture to obtain 0.925 g of γ-lactone of 7α-(2-methylpropyl)-17α-$\Delta^{1,4}$-pregnadiene-17β-ol-3-one-21 carboxylic acid which melted at 245° C. after crystallization from isopropanol and had a specific rotation of $[\alpha]_D^{20} = +6.5° \pm 2°$ (c=0.5% in chloroform).

Analysis: $C_{26}H_{36}O_3$; molecular weight=396.5. Calculated: %C, 78.74; %H, 9.15. Found: %C, 78.9; %H, 9.4.

EXAMPLE 20

γ-lactone of 7α-dimethylaminopropyl-17α-$\Delta^4$-pregnene-17β-ol-3-one-21-carboxylic acid 10.2 g of γ-lactone of $\Delta^{4,6}$-pregnadiene-17β-ol-3-one-21-carboxylic acid (canrenone) were added under an inert atmosphere at room temperature to a solution of 0.810 g of cuprous chloride, 0.510 g of lithium chloride and 210 ml of tetrahydrofuran and after cooling the solution to −30° C., 65 ml of a solution of 0.85 mM/ml of N-dimethylaminopropyl magnesium chloride in tetrahydrofuran were added thereto over 90 minutes. The mixture was held at −30° C. for 30 minutes and then 100 ml of 5N hydrochloric acid were added thereto. After one hour at room temperature, the mixture was made alkaline by addition of 2N ammonium hydroxide solution and the decanted aqueous phase was extracted with ethyl acetate. The organic phase was washed with water, dried and evaporated to dryness. The 12 g of residue were chromatographed over silica gel and was eluted with a 93-7-0.5 methylene chloride-isopropanol-ammonium hydroxide mixturee to obtain 4.8 g of product which was crystallized from ethyl acetate to obtain 2 g of γ-lactone of 7α-dimethylaminopropyl-17α-$\Delta^4$-pregnene-17β-ol-3-one-21-carboxylic acid melting at 166° C. and having a specific rotation of $[\alpha]_D^{20} = +56.5° \pm 1.5°$ (c=1% in chloroform).

Analysis: $C_{27}H_{11}NO_3$; molecular weight=427.608. Calculated: %C, 75.83; %H, 9.67; %N, 3.28. Found: %C, 76.1; %H, 9.8; %N, 3.3.

EXAMPLE 21

γ-lactone of 7α-propyl-19-nor-$\Delta^4$-pregnene-17β-ol-3-one-21-carboxylic acid A mixture of 75 ml of tetrahydrofuran, 101 mg of cuprous chloride and 33 mg of lithium chloride was stirred at 20° C. for 30 minutes and then 2.5 g of the γ-lactone of 19-nor-$\Delta^{4,6}$-pregnadiene-17β-ol-3-one-21-carboxylic acid (obtained in French Pat. No. 2,216,276) were added thereto. The mixture was stirred for 30 minutes and then 12 ml of n-propyl magnesium bromide were added thereto at 10° C. over 30 minutes. The mixture was stirred at 15° C. for 15 minutes and then 15 ml of N hydrochloric acid were added thereto. The mixture was poured into 300 ml of water and was then extracted with ethyl acetate. The organic phase was dried and evaporated to dryness and the residue was chromatographed over silica gel. Elution with a 7-3 benzene-ethyl acetate mixture yielded 1.78 g of γ-lactone of 7α-propyl-19-nor-$\Delta^4$-pregnene-17β-ol-3-one-21-carboxylic acid and 0.38 mg of its 7β-isomer. The 1.78 g of the 7α-isomer were dissolved in 5 ml of methylene chloride and the mixture was concentrated. The mixture was taken up in ether and the mixture was vacuum filtered. The crystals were washed with ether and dried to obtain 1.56 g of 7α-isomer melting at 177° C. and having a specific rotation of $[\alpha]_D^{20} = +27° \pm 2°$ (c=0.6% in chloroform).

Analysis: $C_{24}H_{34}O_3$; molecular weight=370.53. Calculated: %C, 77.80; %H, 9.25 Found: %C, 77.9; %H, 9.3.

NMR Spectrum (deuterochloroform—60 MHz): Peaks at 1.03 ppm (18-methyl); at 5.92 ppm (4-hydrogen).

EXAMPLE 22

Tablets were prepared containing 50 mg of the product of Example 10 and sufficient excipient of talc, starch and magnesium stearate for a final weight of 150 mg.

PHARMACOLOGICAL STUDY

A. Antialdosterone Activity

The study was effected by a test inspired by Kagawa [P.S.E.B.M., Vol. 99 (1958), p. 705] and Marcus [Endocrinology, Vol. 50 (1952), p. 286] in which male rats of the Sprague Dawley SPF IFFA CREDO strain weighing 180 g were surrenalectomized 7 days before diuresis while anestesized with Imalgene (Ketamine) intraperitoneally at a dose of 100 mg/kg. After the operation and from the night before the start of the test, the rats received physiological serum as drinking water and the animals were held without food or drink for 17 hours before diuresis and the physiological serum was replaced by water containing 5% glucose. The test products were orally administered before placing them in a cage and at the moment of diuresis, the animals received intraperitoneally a hydrosaline surcharge of 5 ml per rat of 9°/₀₀ physiological serum and subcutaneously 1 μg/kg of aldosterone monoacetate in 2.5% alcoholic solution.

The rats were placed in pairs in a diuresis cage without food or drink for 4 hours and at this time, a forced emission was induced by pressure against the bladder and the volume of recovered urine was measured. After careful rinsing of the cages and the glass, the urine volume was adjusted to 50 ml and this solution was treated to determine the amount of potassium and sodium in the urine by flame photometry in an autoanalyszer. The results were expressed in the percentage of inhibition of the activity of 1 μg/kg of aldosterone monoacetate injected subcutaneously with the log of the ratio of sodium concentration/potassium concentration by the method of Kagawa [Endocrinology, Vol. 67, (1960), p. 125–132]. The percent of inhibition for the product of Example 10 was 80 and 30% at doses of 2 and 0.4 mg/kg, respectively.

B. Androgenic Activity

The androgenic activity of the product of Example 10 was studied by the hormonal receptor method of Raynaud et al. [J. Ster. Biochem., (1975), p. 615–622] in which the prostate was removed from male rats castrated 24 hours earlier. The latter was homogenized in a buffered solution of 10 mm of tromethamine, 0.25 M of saccharose and a pH of 7.4 with hydrochloric acid. The homogenate was centrifuged at 105,000 g per hour and the surnageant or cytosol was adjusted to a dilution of 1/5 (weight/volume). The resulting solution was incubated at 0° C. for 2 hours in tubes with the same volume of cytosol with a fixed concentration of tritiated 17α-methyl-$\Delta^{4,9,11}$- estratriene-17β-ol-3-one (designated as tritiated Product R) in the presence or not of an increasing concentration of radioinactive 17α-methyl-Δ$^{4,9,11}$-estratriene-17β-ol-3-one (designated as cold product R) or the test product. The radioactivity of the tritiated product R was determined in 2 hours by the technique of adsorption or carbondextran (1.25%–0.625%). The plots were the curves representing the percentage of tritiated product R as a function of the log of the concentration of cold product R or the test product of the I$_{50}$ straight line parallel to the axis of the abcisses and ordinates.

$$B/T = (B/T\,\text{Max.} + B/T\,\text{Min.})/2$$

B/T max. is the percentage of tied tritiated product R when the product is not added and B/T min. is the percentage of tied tritiated product R when the maximum amount of cold product R is added. The intersections of these I$_{50}$ straight lines and the curves permit the determination of the values: CT-concentration of cold 17α-methyl-Δ$^{4,9,11}$-estratriene-17β-ol-3-one which inhibits by 50% the fixation of the tritiated product R and CX-concentration of test product which inhibits by 50% the fixation of tritiated product R. The relative affinity of the test product test (ARL) was determined by the formula $$AR = 100 \times (CT/CX)$$

and the results are reported in the following Table.

TABLE

| Product | ARL |
|---|---|
| Testosterone | 100 |
| Example 10 | 0.02 |

Various modifications of the products and process of the invention may be made without departing from the spirit or scope thereof and it is to be understood that the invention is intended to be limited only as defined in the appended claims.

We claim:

1. A steroids of the formula

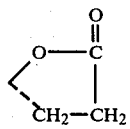

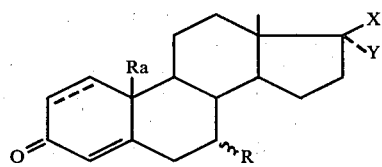

wherein R is selected from the group consisting of R$_1$ and R$_2$, R$_1$ is selected from the group consisting of alkyl of 1 to 8 carbon atoms and alkenyl and alkynyl of 2 to 8 carbon atoms R$_2$ is —(CH$_2$)$_n$—R$_3$ n is an integer from 1 to 8 and R$_3$ is selected from the group consisting of free or protected —OH, free or protected —NH$_2$, monoalkyl and dialkylamino with 1 to 6 carbon atoms, a free, esterified or salified —COOH and halogen X and Y together form

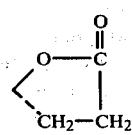

or X is OH and Y is —CH$_2$—CH$_2$—COOM, M is selected from the group consisting of hydrogen, an alkali metal and —NH$_4$, Ra is selected from the group consisting of hydrogen and methyl, the dotted line in the 1(2)-position indicates the optional presence of a double bond and the wavy line indicates that R may be in the α- or β-position, with the proviso that R is not R$_1$ or R$_2$ when n is 1 and R$_3$ is halogen, when the 1(2) bond is a simple bond and when Ra is —CH$_3$, R$_3$ is not a free carboxyl when Y is —CH$_2$—CH$_2$—COOM in which M is an alkali metal or —NH$_4$ and R$_3$ is not a salified carboxyl when Y is —CH$_2$—CH$_2$—COOH.

2. A compound of claim 1 wherein Ra is methyl.

3. A compound of claim 1 wherein Ra is methyl, R is R$_2$ and the bond in the 1(2)-position is a single bond.

4. A compound of claim 1 wherein Ra is hydrogen and the bond in the 1(2)-position is a single bond.

5. A compound of claim 1 wherein the bond in the 1(2)-position is a double bond.

6. A compound of claim 1,3,4 or 5 wherein X and Y are the group

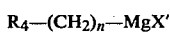

7. A compound of claim 1,3,4 or 5 wherein X is —OH and Y is —CH$_2$—CH$_2$—COOK.

8. A compound of claim 1 wherein R is in the α-position.

9. A compound of cliam 1,2,4,5,6,7 or 8 wherein R is selected from the group consisting of propyl, butyl, isobutyl or butenyl.

10. A compound of claim 1 wherein R is selected from the group consisting of chloropropyl, hydroxypropyl, carboxyethyl and methoxycarbonylethyl.

11. A compound of claim 1 selected from the group consisting of γ-lactone 7α-propyl-17α-Δ$^{1,4}$-pregnadiene-17β-ol-3-one-21-carboxylic acid and potassium 7α-propyl-17α-Δ$^{1,4}$-pregnadiene-17β-ol-3-one-21-carboxylate.

12. A process for the preparation of a compound of claim 1 wherein Ra is methyl comprising reacting a compound of the formula

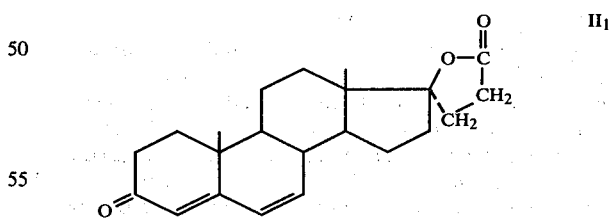

with either a compound of the formula

R$_4$—(CH$_2$)$_n$—MgX'  III$_1$ in the presence of a copper salt wherein X' is a halogen and R$_4$ is selected from the group consisting of protected —OH, protected amino and monoalkylamino and dialkylamino and n is 1 to 8 or with a compound of the formula

[R$_4$—(CH$_2$)$_n$]$_2$ Cu Li  III$_1$' wherein R4 and n have the above definitions to obtain after treatment with an acid a compound of the formula

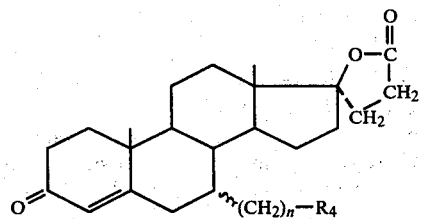  I″A in the form of a mixture of 7α- and 7β-isomers which, if desired, may be separated and, if desired, each isomer or the mixture thereof when R4 is protected —OH or protected amino may be treated with a hydrolysis agent to obtain a compound of the formula

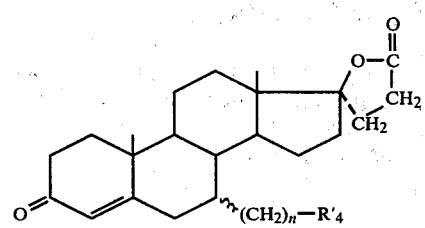  I″B wherein R4′ is selected from the group consisting of —OH and —NH2 and when R4′ is —OH, reacting the compound of formula I_B″ with an oxidizing agent to obtain a compound of the formula

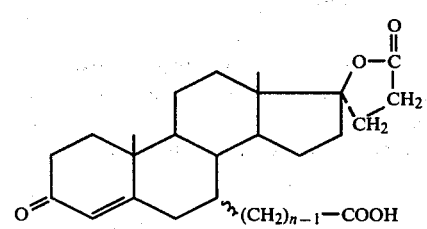  I″C which may be esterified or salified by known methods or when n is other than 1, the compound of formula I_B″ is reacted with a halogenation agent to obtain a compound of the formula

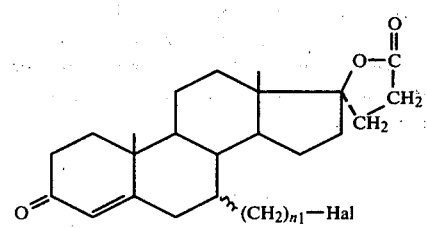  I″D wherein $n_1$ is a integer from 2 to 8 Hal is a halogen and, if desired, the compounds of formulae $I_A″$, $I_B″$, $I_C″$ or $I_D″$ in their 7α- or 7β-isomer form or mixtures thereof may be reacted with an alkali metal hydroxide or ammonium hydroxide to obtain a compound of the formula

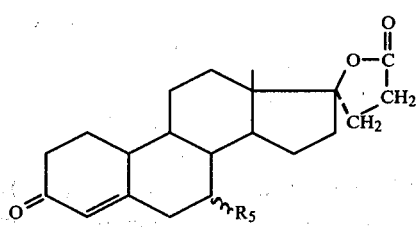 I″T wherein $R_3′$ is $R_3$ other than free carboxy and M′ is an alkali metal or —NH4 in the form of its 7α- or 7β-isomers or mixtures thereof which, if desired, may be separated and then reacting the same with an acid agent to obtain a compound of the formula

I″U wherein $R_3″$ is $R_3$ other than salified carboxy.

13. A process for the preparation of a compound of claim 1 wherein Ra is hydrogen comprising reacting a compound of the formula

II2 with either a compound of the formula

R5—Mg—X′    III2 in the presence of a copper salt wherein R5 is R1 or R4—(CH2)n— and X′ is a halogen or with a compound of the formula (R5)2CuLi    III2′ to obtain after treatment with an acid a compound of the formula

I″A1 in the form of its 7α- and 7β-isomers which, if desired, may be separated and, if desired, each isomer or a mixture thereof when R5 is —(CH2)n—R4 and R4 is a protected amino or protected —OH reacted with a hydrolysis agent to obtain a compound of the formula

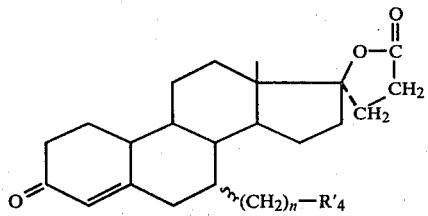

wherein R₄' is —OH or —NH₂ and reacting a compound of formula I"_{B1} wherein R₄ is —OH with either an oxidation agent when n is greater than 1 to obtain a compound of the formula

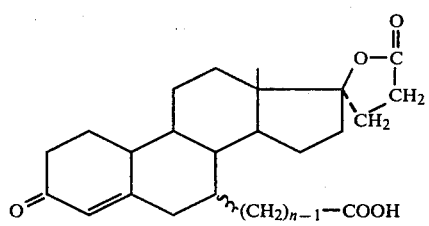

which is optionally esterfied or salified by known methods or reacting the compound of formula I"_{B1} with a halogenation agent to obtain a compound of the formula

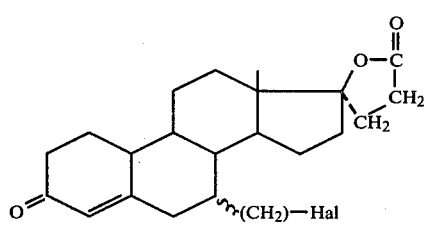

wherein Hal is a halogen and, if desired, reacting the compounds of formulae I"_{A1}, I"_{B1}, I"_{C1} or I"_{D1} in the form of their 7α- or 7β-isomers or mixtures thereof with an alkali metal hydroxide or ammonium hydroxide to obtain a compound of the formula

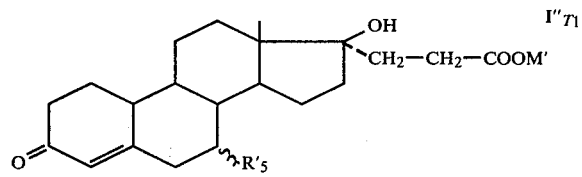

wherein R₅' has the definition of R₁ or is —(CH₂)ₙ—R₃' wherein R₃' is R₃ with the exception of free carboxyl and M' is alkali metal or —NH₄' or the form of its 7α- or 7β-isomers or mixtures thereof which can be separated into its isomers if desired and subjecting the compound of formula I"_{T1} to an acid agent to obtain a compound of the formula

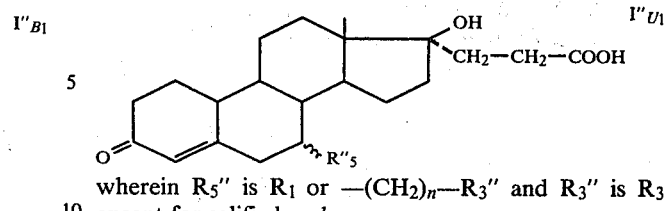

wherein R₅" is R₁ or —(CH₂)ₙ—R₃" and R₃" is R₃ except for salified carboxy.

14. A process for the preparation of a compound of claim 1 wherein the bond in the 1(2)-positon is a double bond comprising reacting a compound of the formula

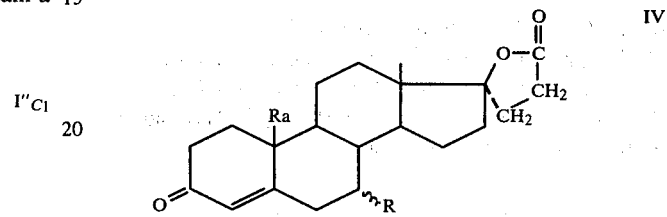

wherein R is R₁ or R₂ and Ra, R₁ and R₂ have the above definitions in the form of its 7α- or 7β-isomers or mixtures thereof with a dehydrogenation agent to obtain a compound of the formula

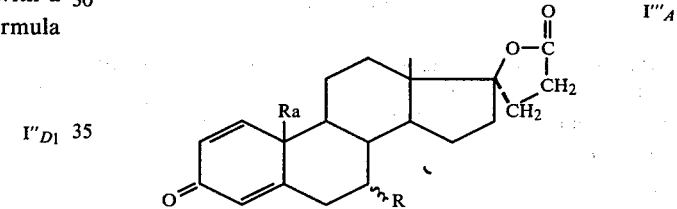

in the form of its 7α- or β-isomers or mixtures thereof which an optionally be separated and reacting the latter with an alkali metal hydroxide or ammonium hydroxide to obtain a compound of the formula

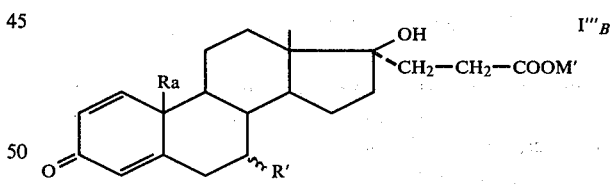

wherein M' is an alkali meta or —NH₄ and R' is R except for free carboxy in the form of its 7α- or 7β-isomers or mixtures thereof which, if desired, may be separated and subjecting the latter to an acid agent to form a compound of the formula

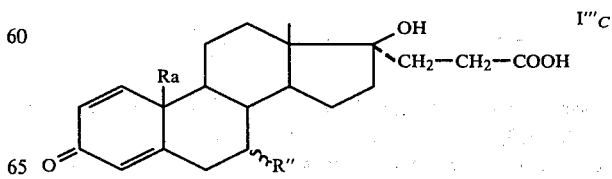

wherein R" is R except for (CH₂)ₙ—R₃ and R₃ is salified carboxy.

15. A composition for treating cardiac insufficiency and arterial hypertension comprising an amount of at least one compound of claim 1 sufficient to combat arterial hypertension and cardiac insufficiency and an inert pharmaceutical carrier.

16. The compositions of claim 15 wherein Ra is methyl.

17. The composition of claim 15 wherein Ra is methyl, R is R₂ and the bond in the 1(2)-position is a single bond.

18. The composition of claim 15 wherein Ra is hydrogen and the bond in the 1(2)-position is a single bond.

19. The composition of claim 15 wherein the bond in the 1(2)-position is a double bond.

20. The composition of claim 15 wherein X and Y are the group

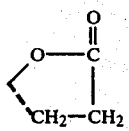

21. The composition of claim 14 wherein X is —OH and Y is —CH₂—CH₂—COOK.

22. The composition of claim 14 wherein R is in the α-position.

23. The composition of claim 14 wherein R is selected from the group consisting of propyl, butyl, isobutyl and butenyl.

24. The composition of claim 14 wherein R is R₂ which is selected from the group consisting of chloropropyl, hydroxypropyl, carboxyethyl and methoxycarbonylethyl.

25. A composition of claim 15 wherein the compound is selected from the group consisting of γ-lactone of 7α-propyl-17α-Δ¹,⁴-pregnadiene-17β-ol-3-one-21-carboxylic acid and potassium 7α-propyl-17α-Δ¹,⁴-pregnadiene-17β-ol-3-one-21-carboxylate.

26. A method of treating cardiac insufficiency and arterial hypertension in warm-blooded animals comprising administering to warm-blooded animals an amount of at least one compound of claim 1 sufficient to treat arterial hypertension and cardiac sufficiency.

27. The method of claim 26 wherein Ra is methyl.

28. The method of claim 26 wherein Ra is methyl, R is R₂ and the bond in the 1(2)-position is a single bond.

29. The method of claim 26 wherein Ra is hydrogen and the bond in the 1(2)-position is a single bond.

30. The method of claim 26 wherein the bond in the 1(2)-position is a double bond.

31. The method of claim 26 wherein X and Y are the group

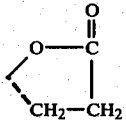

32. The method of claim 26 wherein X is —OH and Y is —CH₂—CH₂—COOK.

33. The method of claim 26 wherein R is in the α-position.

34. The method of claim 26 wherein R is selected from the group consisting of propyl, butyl, isobutyl and butenyl.

35. The method of claim 26 wherein R is R₂ which is selected from the group consisting of chloropropyl, hydroxypropyl, carboxyethyl and methoxycarbonylethyl.

36. The method of claim 26 wherein the compound is selected from the group consisting of the γ-lactone of 7α-propyl-17α-Δ¹,⁴-pregnadiene-17β-ol-3-one-21-carboxylic acid and potassium 7α-propyl-17α-Δ¹,⁴-pregnadiene-17β-ol-3-one-21-carboxylate.

* * * * *

UNITED STATES PATENT AND TRADEMARK OFFICE
CERTIFICATE OF CORRECTION

PATENT NO. : 4,396,614

DATED : August 2, 1983

INVENTOR(S) : LUCIEN NEDELEC ET AL.

Page 1 of 2

It is certified that error appears in the above-identified patent and that said Letters Patent is hereby corrected as shown below:

Title page, the second structural formula of the Abstract should read

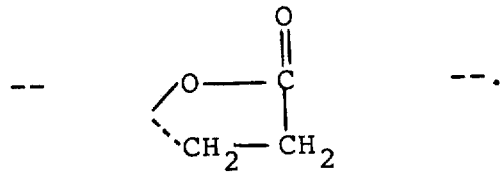

Column 2, lines 17 and 66; Column 9, line 30:
" -CH-" should read -- $-CH_2-$ --.

Column 2, lines 18 and 67; Column 9, line 31: Delete "$_2-$"

Column 2, line 53: "Rα" should read -- Ra --.

Column 6, line 60: "$R_5''$" should read -- $R_5'$ --.

Column 7, line 31: "$I_c'$ " should read -- $I_c''$ --.

Column 9, line 2: "emulsins" should read -- emulsions --.

Column 9, line 7: After "origin" insert a comma -- , --.

Column 9, line 48: "in 0.05" should read -- is 0.05 --.

Column 10, line 60: "cyrstallized" should read -- crystallized --.

Column 11, line 20: "bicaronate" should read -- bicarbonate --.

Column 14, line 6: "{-lactone" should read -- γ-lactone --.

Column 14, line 20: "-20°35 1°" should read -- -20° ± 1° --.

Column 14, line 51: "$[\Delta]_D^{20}$" should read -- $[\alpha]_D^{20}$ --

Column 14, line 66: "325°C" should read -- 235°C --.

Column 15, line 15: "$[\alpha_D^{20}$" should read -- $[\alpha]_D^{20}$ --

UNITED STATES PATENT AND TRADEMARK OFFICE
CERTIFICATE OF CORRECTION

PATENT NO. : 4,396,614
DATED : August 2, 1983
INVENTOR(S) : LUCIEN NEDELEC ET AL.

Page 2 of 2

It is certified that error appears in the above-identified patent and that said Letters Patent is hereby corrected as shown below:

Column 17, line 35: "mixturee" should read -- mixture --.
Column 19, line 12: "B/T = (B/T Max. + B/T Min.)/2" should read $$\frac{B}{T} = \frac{B/T \text{ Max.} + B/T \text{ Min.}}{2}$$

Column 19, line 28: "AR = 100 x (CT/CX)" should read $$AR = 100 \times \frac{CT}{CX}$$

Column 24, line 53: "meta" should read -- metal --.
Column 25, line 3: "clam" should read -- claim --.
Column 25, line 1 of claims 21, 22, 23 and 24:
"claim 14" should read -- claim 15 --.

Signed and Sealed this

Seventh Day of February 1984

[SEAL]

Attest:

GERALD J. MOSSINGHOFF

Attesting Officer

Commissioner of Patents and Trademarks